United States Patent
Puskas et al.

(10) Patent No.: US 9,572,561 B2
(45) Date of Patent: Feb. 21, 2017

(54) STERNAL RETRACTOR

(71) Applicant: Emory University, Atlanta, GA (US)

(72) Inventors: John D. Puskas, Atlanta, GA (US); Kelly Kloster Hon, Johns Creek, GA (US); Erick Eladio Rios, New Haven, CT (US); Brian Wong-Shui, Atlanta, GA (US); Mark Joseph Moneypenny, New Haven, CT (US)

(73) Assignee: EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 14/030,606

(22) Filed: Sep. 18, 2013

(65) Prior Publication Data

US 2014/0128683 A1 May 8, 2014

Related U.S. Application Data

(63) Continuation-in-part of application No. 13/786,370, filed on Mar. 5, 2013.

(60) Provisional application No. 61/690,662, filed on Jul. 2, 2012.

(51) Int. Cl.
*A61B 17/02* (2006.01)
*A61B 1/32* (2006.01)

(52) U.S. Cl.
CPC ............. *A61B 17/0206* (2013.01); *A61B 1/32* (2013.01)

(58) Field of Classification Search
CPC ............................ A61B 17/0206; A61B 1/32
See application file for complete search history.

(56) References Cited

U.S. PATENT DOCUMENTS

| | | | |
|---|---|---|---|
| 1,613,141 A * | 1/1927 | Stein | 600/232 |
| 4,627,421 A | 12/1986 | Symbas et al. | |
| 4,726,356 A | 2/1988 | Santilli et al. | |
| 4,829,985 A | 5/1989 | Couetil | |
| 4,852,552 A | 8/1989 | Chaux | |
| 4,865,019 A | 9/1989 | Phillips | |
| 4,989,587 A | 2/1991 | Farley | |
| 5,067,477 A | 11/1991 | Santangelo | |
| 5,088,472 A | 2/1992 | Fakhrai | |

(Continued)

FOREIGN PATENT DOCUMENTS

| | | |
|---|---|---|
| DE | 202011051999 | 11/2011 |
| WO | 9909892 | 3/1999 |

(Continued)

OTHER PUBLICATIONS

Jain, Sanjay M., "Sternal Retractor for Internal Mammary Artery", The Annals of Thoracic Surgery 62:908-909 (1996).

(Continued)

*Primary Examiner* — Andrew Yang
(74) *Attorney, Agent, or Firm* — Parks IP Law LLC; Stephen J. Terrell

(57) ABSTRACT

Devices and methods for sternal retraction that reduces bleeding from the cut edges of a sternum and reduces fracturing of the sternum during retraction. The devices and methods involve the use of sternal retractor blades having a certain geometry and inserts placed inside the sternal retractor blades during retraction of the sternotomy incision. The blades and inserts act to tamponade the blood flow from the cut sternal edge and reduce fracturing of the sternum during retraction.

23 Claims, 9 Drawing Sheets

(56) References Cited

U.S. PATENT DOCUMENTS

| | | | |
|---|---|---|---|
| 5,159,921 A | 11/1992 | Hoover | |
| RE34,150 E | 12/1992 | Santilli et al. | |
| 5,167,223 A | 12/1992 | Koros et al. | |
| 5,512,038 A | 4/1996 | O'Neal et al. | |
| 5,772,583 A | 6/1998 | Wright et al. | |
| 5,779,629 A | 7/1998 | Hohlen | |
| 5,788,630 A | 8/1998 | Furnish | |
| 5,846,194 A | 12/1998 | Wasson et al. | |
| 5,976,171 A | 11/1999 | Taylor | |
| 5,984,867 A | 11/1999 | Deckman et al. | |
| 6,033,425 A | 3/2000 | Looney et al. | |
| 6,099,468 A | 8/2000 | Santilli et al. | |
| 6,102,854 A | 8/2000 | Cartier et al. | |
| 6,149,584 A | 11/2000 | Raju | |
| 6,206,828 B1 | 3/2001 | Wright | |
| 6,254,533 B1 | 7/2001 | Fadem et al. | |
| 6,273,853 B1 | 8/2001 | Cartier et al. | |
| 6,283,912 B1 | 9/2001 | Hu et al. | |
| 6,312,377 B1 | 11/2001 | Segermark et al. | |
| 6,322,500 B1 | 11/2001 | Sikora et al. | |
| 6,348,036 B1 | 2/2002 | Looney et al. | |
| 6,361,492 B1 | 3/2002 | Santilli | |
| 6,371,911 B1 | 4/2002 | Hossain et al. | |
| 6,416,469 B1 | 7/2002 | Phung et al. | |
| 6,416,470 B2 | 7/2002 | Paolitto et al. | |
| 6,440,064 B1 | 8/2002 | Rehm | |
| 6,475,142 B1 | 11/2002 | Parsons et al. | |
| 6,478,733 B1 | 11/2002 | Weinstein et al. | |
| 6,500,116 B1 | 12/2002 | Knapp | |
| 6,517,563 B1 | 2/2003 | Paolitto et al. | |
| 6,547,725 B1 | 4/2003 | Paolitto et al. | |
| 6,599,240 B2 | 7/2003 | Puchovsky et al. | |
| 6,648,818 B2 | 11/2003 | Cartier et al. | |
| 6,758,808 B2 | 7/2004 | Paul et al. | |
| 6,896,654 B2 | 5/2005 | Paolitto et al. | |
| 2,979,291 A1 | 12/2005 | Phillips et al. | |
| 7,011,628 B2 * | 3/2006 | LiDonnici | 600/210 |
| 7,220,228 B2 | 5/2007 | Hu et al. | |
| 7,276,024 B1 | 10/2007 | Royse et al. | |
| 7,294,103 B2 | 11/2007 | Bertolero et al. | |
| 7,507,202 B2 | 3/2009 | Schoellhorn | |
| 7,824,332 B2 | 11/2010 | Fakhrai | |
| 7,883,462 B2 | 2/2011 | Hamman et al. | |
| 7,985,179 B2 | 7/2011 | Gephart et al. | |
| 2004/0225197 A1 | 11/2004 | Roux et al. | |
| 2005/0096508 A1 | 5/2005 | Valentini et al. | |
| 2005/0165445 A1 * | 7/2005 | Buckman et al. | 606/213 |
| 2007/0179345 A1 | 8/2007 | Santilli | |
| 2008/0215054 A1 | 9/2008 | Wright | |

FOREIGN PATENT DOCUMENTS

| | | |
|---|---|---|
| WO | 0176505 | 10/2001 |
| WO | 0180725 | 11/2001 |
| WO | 2004084707 | 10/2004 |

OTHER PUBLICATIONS

International Application No. PCT/US20131029203 Search Report and Written Opinion (Jun. 21, 2013).

International Application No. PCT/US20131060407 Search Report and dated Dec. 19, 2013.

Supplemental Search Report in related European Application No. 13761715.5, dated Feb. 16, 2016.

* cited by examiner

STERNAL RETRACTOR

CROSS REFERENCE TO RELATED APPLICATIONS

This application is related to U.S. application 61/609,662 filed on Mar. 12, 2012, and U.S. application Ser. No. 13/786,370 filed on Mar. 5, 2013, both of which are hereby incorporated by reference.

BACKGROUND OF THE INVENTION

The present invention relates generally to medical devices, and more specifically to a sternal retractor that minimizes blood loss and fractures of the sternum during use of the sternal retractor.

Approximately 1,000,000 cardiac surgical procedures are performed worldwide each year. In the vast majority (>95%) of these procedures, access to the heart is achieved by dividing the sternum, a procedure known as a sternotomy. The sternum is the "breast bone", a flat bone approximately 15 to 25 cm in length, 2 to 3 cm in width, and 8 to 16 mm in thickness. In fact, it consists of three bones connected by fused "joints": the manubrium is 3 to 6 cm long and is located at the cephalad end, the sternum proper is 12 to 15 cm long, while the xiphoid is 1 to 4 cm long and located at the caudal end. The manubrium and sternum are composed of thin (1 to 2 mm) outer and inner tables of cortical bone and a wafer-like, spongiform center of cancellous bone in which the bone marrow resides. Within this bone marrow are numerous venous sinusoids.

Bleeding from the cut sternal edges during a sternotomy can be profuse and prolonged, lasting the duration of the operation, which may be 4 to 8 hours. Cardiac surgical patients are usually given a powerful intravenous anticoagulant, heparin, which prevents the formation of clots during the operation. Total blood loss from the sternal marrow frequently exceeds one liter during a cardiac operation. In conventional operations performed with the use of the heart-lung machine, this shed blood is suctioned up into the venous reservoir of the heart-lung machine and then re-infused into the arterial system of the patient. Fat droplets and other particulate matter is copious within blood shed from bone marrow and these "impurities" are also re-infused into the patient, where they have been implicated as a cause of neurocognitive decline (brain injury), respiratory insufficiency, and renal failure after heart surgery. Recent reports in the literature have advocated discarding this shed blood, yet the sheer volume of blood shed from the sternal bone marrow makes this impractical in most cases. Alternatively, this shed blood may be "washed" in a centrifugal cell scavenge system prior to re-infusing the red blood cell portion. Unfortunately, all other blood components (platelets, coagulation proteins, serum proteins, etc.) are wasted in this system and derangements in the normal clotting ability of the patient often result. In either case, the volume of blood routinely shed from the sternum during cardiac surgery is a major cause of blood transfusion during and after cardiac surgery.

Transfusion associated with cardiac surgery is the single largest civilian demand for blood transfusion worldwide. Within the US, cardiac surgery consumes 10 to 15% of all blood provided by the Red Cross. Thus, there is a clear and immediate need for a way to safely reduce the volume of blood shed from sternal bone marrow during surgical procedures performed via sternotomy.

When the surgeon performs a sternotomy to access the heart or other mediastinal structures, the cut edges of the sternum are typically pried apart with a mechanical device known as a sternal retractor. This device is typically made of stainless steel and includes left and right arms and a rack and pinion mechanism to move the arms apart or together. The arms have blades attached thereto, which actually contact or grip the cut edges of the sternum to apply the opening pressure exerted by the rack and pinion. While these blades are currently available in different shapes and sizes to accommodate the numerous different available retractor systems, none are designed to reduce or prevent bleeding from the edges of the sternum.

Another issue with presently used sternal retractors is the issue of sternal fractures. Presently available blades only contact the central or middle region of the sternal edge. This applies a large amount of pressure against a relatively small surface area of the sternum, which leads to frequent fractures of the sternal edges. These fractures contribute to increased sternal bleeding and are associated with delayed or incomplete healing and increased risk of sternal wound infection.

Accordingly, there is a need for a sternal retractor that reduces bleeding from the cut sternal edge and that reduces fracture of the sternum.

SUMMARY OF THE INVENTION

In one aspect the present invention provides a device and method to reduce bleeding from a cut sternal edge during surgery performed via a sternotomy. In another aspect, the present invention provides a device and method to reduce sternal breakage during surgery performed via a sternotomy.

A typical sternal retractor has arms that attach to a rack, wherein one of the arms is fixed and the other is movable via a rack and pinion mechanism. Each arm carries a blade and the blades have sternal engaging surfaces facing away from each other. During a sternotomy, after the cutting of the sternum, the blades are inserted into the chest incision so that they rest against the sternal edges. The rack and pinion is engaged, causing the blades to move away from each other, and forcing the sternal edges to move away from each other. This is continued until a sternal opening is created that is large enough for the surgeon to access the inside of the chest.

The present device and method for reducing bleeding from the cut edges of a sternum involves the use of sternal retractor blades having a certain geometry. The blades act to tamponade the blood flow from the cut sternal edge.

The present device and method for reducing bleeding from the cut edges of a sternum further optionally involves the use of inserts placed inside the sternal retractor blades during retraction of the sternotomy incision. The inserts preferably conform to the surface of the cut sternal bone and act to tamponade the blood flow from the cut sternal edge.

The present device and method for reducing the incidence of sternal fractures during surgical procedures performed via a sternotomy involves the use of sternal retractor blades which extend substantially the length of the sternum and distribute force across substantially the entire sternum during the sternotomy. Because the force applied to the cut sternum is more evenly distributed across the cut edge, the incidence of sternal fracture is reduced. In addition, the present device and method provide a means to create a trapezoidal opening of the sternal cavity, with a wider opening at the caudal end, which also reduces fractures.

In a preferred embodiment, the inserts of the invention are used in retractor blades which extend substantially the length of the sternal edge. In a further preferred embodiment, the retractor blades are configured to fit the shape of the cut sternal edge. In a still further preferred embodiment, the inserts are configured to fit the shape of the cut sternal edge. In a preferred embodiment, the retractor provides a trapezoidal opening of the sternal cavity.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

DETAILED DESCRIPTION OF THE INVENTION

A typical sternal retractor has arms that attach to a rack, wherein one of the arms is fixed and the other is movable via a rack and pinion mechanism. Each arm carries a blade and the blades have sternal engaging surfaces facing away from each other. During a surgical procedure performed via a sternotomy, after the sternum is cut, the blades are inserted into the cut opening so that they rest against the sternal edges. The rack and pinion is engaged, causing the blades to move away from each other and causing the sternal edges to move away from each other. This is continued until a sternal opening is created that is large enough for the surgeon to access the inside of the chest.

The present invention is a sternal retractor that reduces bleeding from the cut edges of the sternum. The present invention also is a sternal retractor that reduces breakage or fracture of the sternum.

Note that while the present invention is described as relating to a sternal retractor having two arms, one of which is fixed and the other movable, the invention is applicable to other types of retractors and retractors having different configurations of arms. For example, the sternal retractor could have two movable arms.

Figure 1:
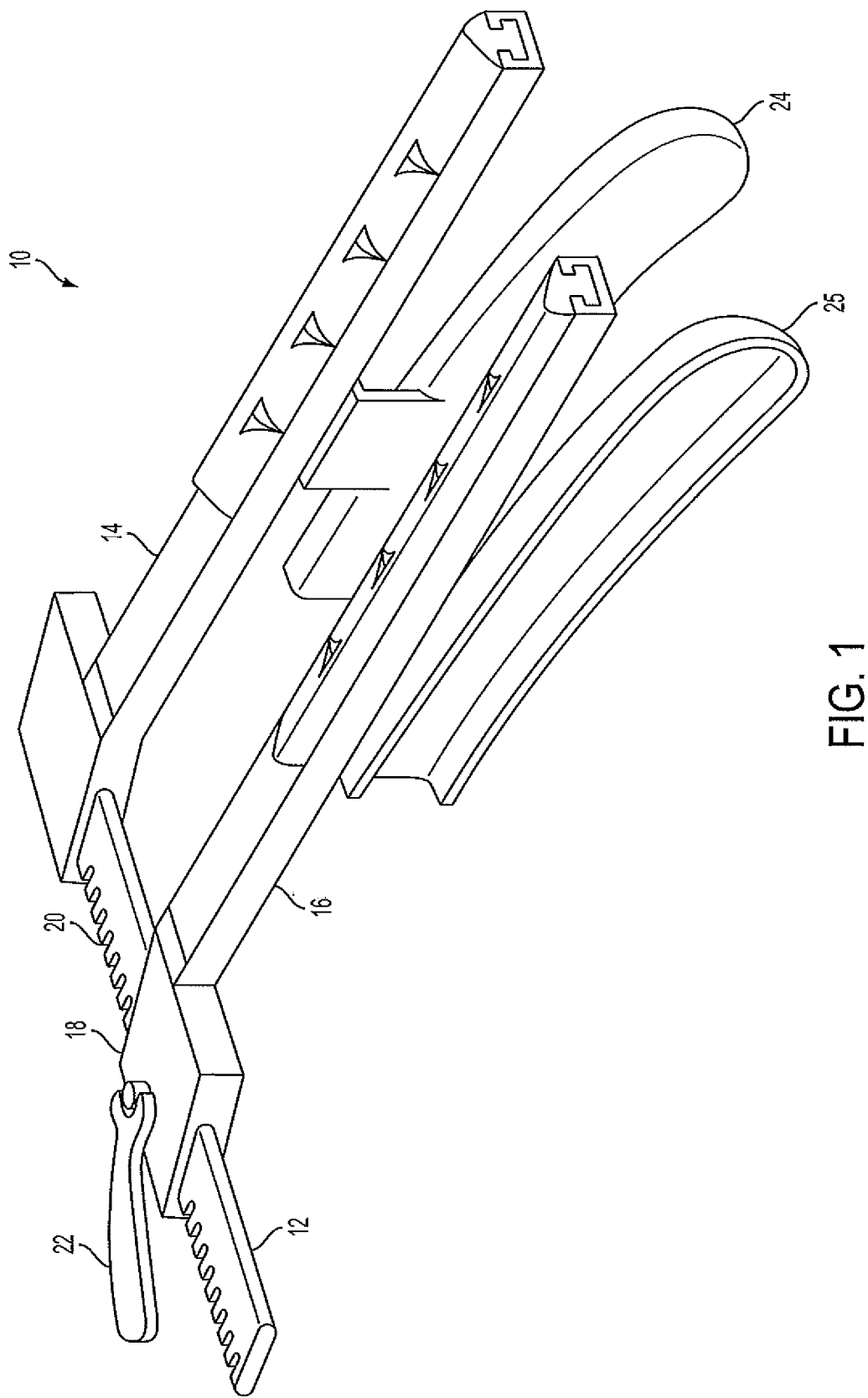
FIG. 1 is a perspective view of a retractor according to one embodiment of the invention.

FIG. 1 illustrates a first embodiment of a sternal retractor according to the invention. The retractor 10 includes a rack 12 having a fixed arm 14 attached thereto. The rack 12 has a second movable arm 16 also connected thereto. Movable arm 16 has a housing 18 on one end thereof containing a pinion gear (not shown). This pinion gear interacts with a number of teeth 20 on rack 12, functioning as a rack and pinion gear. Rotation of the pinion gear and thus movement of the moving arm 16 along the rack 12 is controlled by knob 22.

Retractor blades 24, 25 are attached to the fixed arm 14 and the moving arm 16, respectively. As shown more clearly in FIG. 2, retractor blade 25 includes a rigid frame 26 and an attachment clip 28. A connector 30 connects the attachment clip 28 to the rigid frame 26. The frame, connector, and attachment clip can be one integral part, two separate parts, or three separate parts. Desirably the two blades 24, 25 are mirror images of each other or they can be different.

Rigid frame 26 is sized and shaped to cover a substantial amount of the cut sternal edge. A substantial amount means that the frame extends the entire length of or at least 50% the length of the cut sternal edge. In a more preferred embodiment, the rigid frame covers at least 75% (and up to or over 100%) of the sternal edge. Desirably, rigid frame 26 has a "canoe" shape with a floor 32 and two side walls 34, 36 which substantially encase the cut sternal edge. Desirably frame 26 includes a closed cephalad end 38 and an open caudal end 40. However, the caudal end may also be closed in some embodiments. Floor 32 can be flat or slightly bowed outward or inward.

Since the rigid frame 26 is sized and shaped to cover a substantial amount of the cut sternal edge, its preferred size and shape depends upon the size and shape of the individual patient. It may be desirable to provide a variety of blades with differently sized and shaped rigid frames. In general however, the rigid frame 26 desirably has a length from about 7 cm to 25 cm. The rigid frame 26 desirably has a width (from side wall 34 to side wall 36) between about 1 cm and 3.5 cm. Side walls 34 and 36 are desirably about 0.25 to 2.5 cm high. Side walls 34, 36 can be a consistent height along their lengths or varying heights and can be the same height or different from each other.

The cephalad end 38 can be closed with a wall that is the same height as the side walls 34, 36. Alternatively, the cephalad end 38 can have a lower wall or can be open with no wall. In one embodiment, the cephalad end has a notch (not shown) on the floor 32. The purpose of the closed end 38 or notch is three-fold; first, to signify to the surgeon or other operator that the blade has been inserted and positioned properly; second, to aid in tamponading bleeding from the cut edge of the manubrium; and third, to prevent the retractor blades from sliding caudad when force is applied to them during trapezoidal opening of the sternotomy incision. As described below, during use the closed end 38 or notch provides a signal that the frame 26 has been placed over the cephalad end of the cut sternal edge.

Since the angle between the sternum and manubrium (the Angle of Louis) is slightly bent downwards at the cephalad section, the frame 26 is desirably slightly bent at the cephalad end. Desirably, this angle of curvature between the caudal section and the cephalad section is from about 5 to 30 degrees. Desirably the caudal section is about 4 to 20 cm in length and the cephalad section is about 3 to 5 cm in length. The frame may be wider at the cephalad section than the caudal section, to accommodate the greater thickness of the manubrium.

Blades 24, 25 are attached to the retractor arms 14, 16 via one of a number of mechanisms. Blade 24 or 25 can simply be bolted to the arm 14 or 16 through mating holes in the arm and attachment clip 28. Preferably however, blades 24 and 25 are able to pivot. The sternum is more resistant to spreading at the cephalad end, and if the same force is applied across the entire length of blade frame 26 then the cephalad section is more prone to breaking. Having blades that pivot allows the retractor to open the sternum trapezoidally, wider at the caudal section where the force needed to open the sternum is lower. Desirably the blades pivot at about 5 to 45 degrees. In a preferred embodiment, the caudal aspects of the blades pivot 10 to 30 degrees outwards from the centerline of the retractor.

Figure 3:
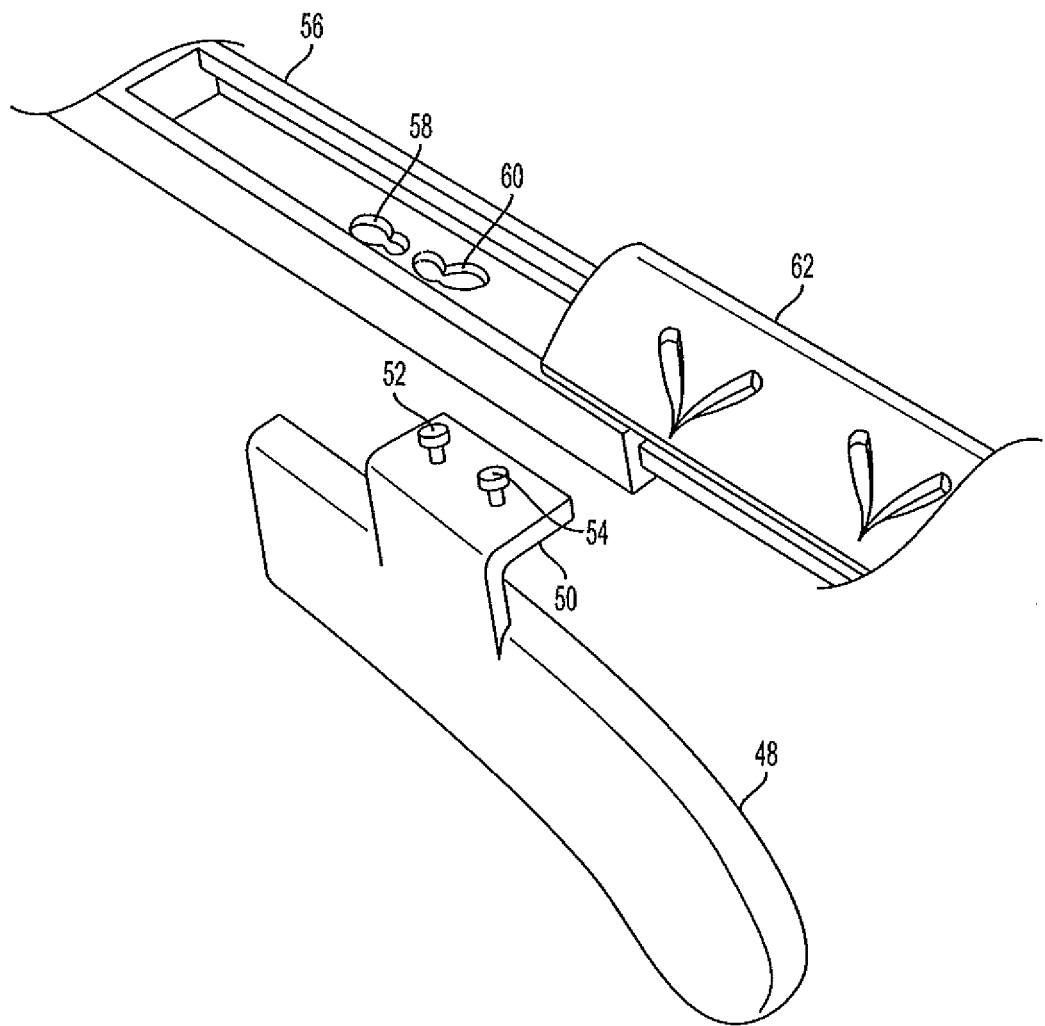
FIG. 3 is an exploded view of one embodiment of the invention illustrating a pivot attachment of the blade to a retractor arm.

Blades 24, 25 are thus preferably attached to the retractor arms 14, 16 with a pivot attachment. This can be a single attachment point, such as a single rotating pin extending through both the blade attachment clip 28 and the arm 14, 16 (and which can also function as the connector 30). Alternately, the blades can be attached with the mechanism shown in FIG. 3, in which the blade attachment clip 50 has two pins 52 and 54 extending therefrom. The pins have expanded heads 53, 55. The retractor arm 56 has two corresponding receiving holes, one of which is a circular stationary receiving hole 58 and the other is an oblong shaped sliding hole 60. The oblong sliding hole 60 is positioned more cephalad and the stationary hole 58 is positioned more caudal. Each of 58 and 60 has a second hole 59, 61, respectively, connected thereto through which the heads 53, 55, respectively can pass. The heads 53, 55 cannot pass through holes 58, 60. The pins 52 and 54 are positioned in the holes 58 and 60, respectively, by inserting pins 52, 54 through holes 59, 61 and then sliding the pins into holes 58, 60.

The blade 48 will pivot when the pin 54 slides in the sliding receiving hole 60. The range of pivot of the blade is restricted by the length of the sliding receiving hole 60. The blade 48 is kept in place by the pin heads 53, 55 and using a sliding stitch guide 62 that slides into a groove 64 of the retractor arm 56, thus holding the pins 52 and 54 into position.

Figure 4:
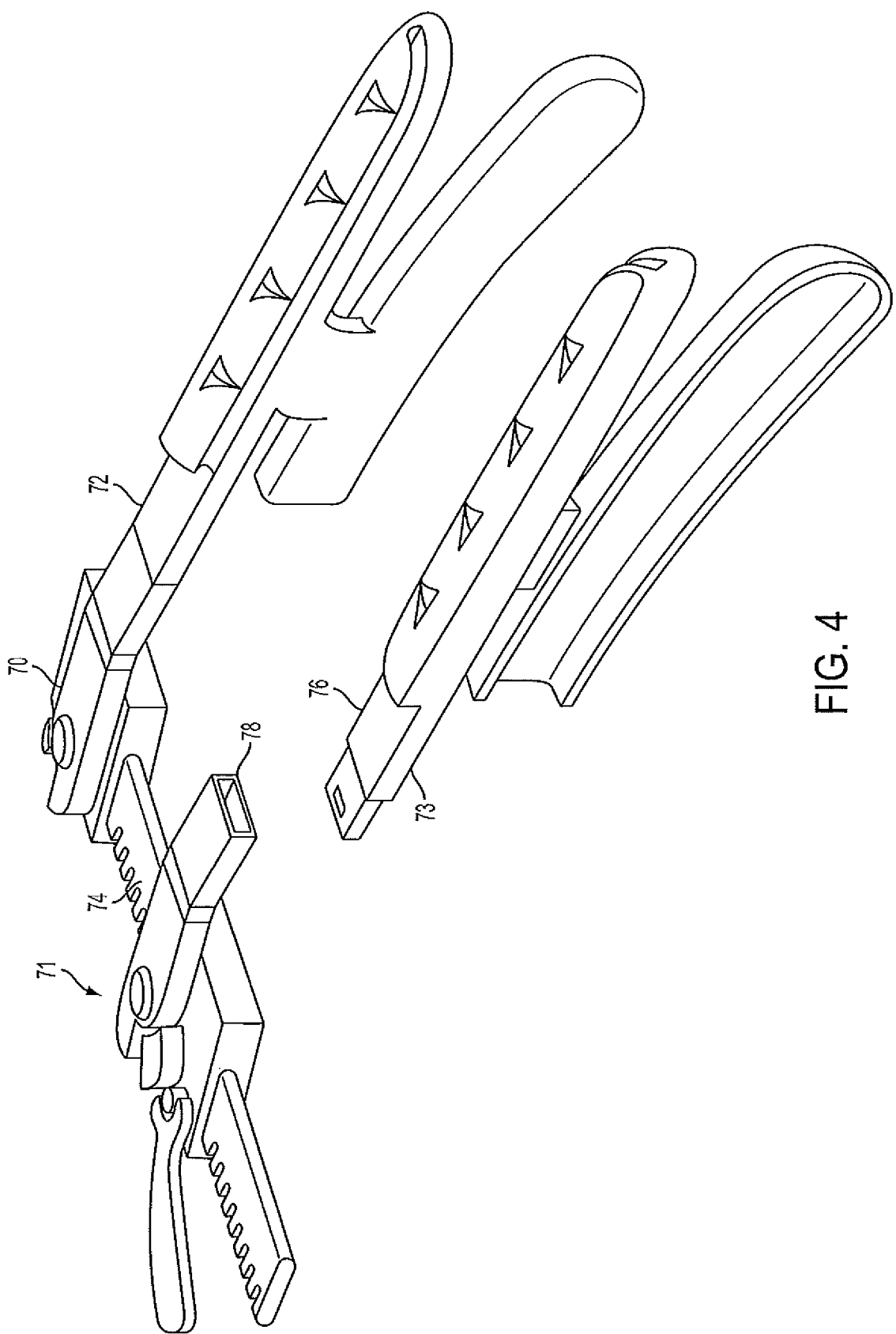
FIG. 4 is a view of an embodiment of the invention illustrating pivoting retractor arms.

In another embodiment, trapezoidal opening of the sternum is provided by pivoting retractor arms. As shown in FIG. 4, pivot mechanisms 70 and 71 attach the retractor arms 72 and 73 to the rack 74. Retractor arm 73 is a two piece assembly 76, 78 which snaps together and arm 72 preferably has the same configuration.

Figure 5:
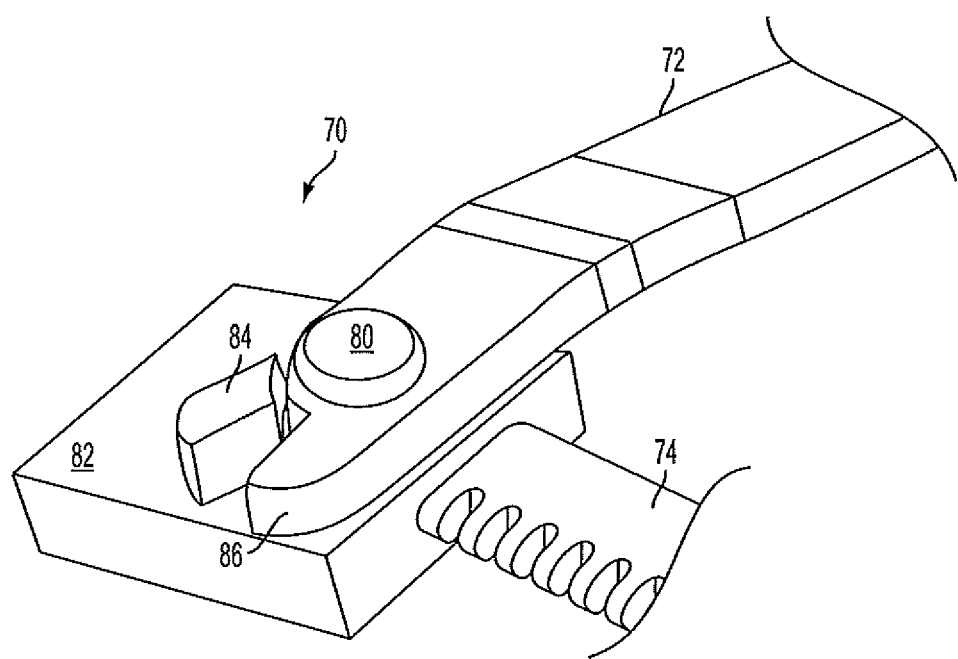
FIG. 5 illustrates the pivot attachment shown in FIG. 4 in greater detail.

FIG. 5 illustrates the pivot attachment 70 in greater detail. A pin 80 rotatably fastens arm 72 to the housing 82. A fixed or adjustable pawl 84 mechanically stops the rotation of the arm 72 at the desired angle when it meets tab 86 on the end of retractor arm 72. When the retractor blades are inserted into the sternotomy incision the blades are parallel and as the retractor opens the angle of the retractor arm 72 can change until tab 86 hits the pawl 84. FIG. 5 shows the pawl 84 allowing a range of motion of the arms 72 and 73 from 0 to 25°. The pawl however can allow a range of motion up to about 45°.

Desirably, the pivot mechanisms described above or otherwise provided are equipped with an adjustable governor mechanism that allows the surgeon to adjust the desired range of motion of the retractor arms and/or blades either before insertion of the retractor blades into the chest or after insertion, during the spreading of the retractor arms. Desirably this governor allows a range of motion of the arms or blades between about 0 and 45°.

In another embodiment, to provide for a trapezoidal sternal opening, the blades can be nonpivoting and the rack can be curved in the cephalad/caudal direction, so that as the retractor arms are spread the blades open the sternum at an angle defined by the curvature of the rack. Desirably, in this embodiment, the rack would be curved such that S linear inches of the rack allow for about 10 to 30 degrees of arc.

In addition to allowing for distribution of pressure across the sternum, the trapezoidal sternal opening provided by pivoting blades or arms applies reduced pressure on the clavicles and brachial plexus (a very important set of nerves in the shoulder that innervate the arm). When the sternum is opened the same amount at the manubrium as at the bottom (xiphoid), in a rectangular fashion, excess pressure may be placed on the brachial plexus, which can cause neuropraxia of the brachial plexus.

In yet another embodiment, the rack can be bent in the antero-posterior direction at about 10 to 30 degrees, so that it conforms to the rounded anterior surface of the human chest and abdomen. This optional aspect is shown in FIG. 1. Of course, the rack may be both curved in the cephalad/caudal direction and bent in the antero-posterior direction. Another optional feature that further provides for beneficial shaping of the retractor to the patient's torso is a slight downward angling of the retractor arms. This feature is illustrated in FIGS. 1 and 4.

In another set of preferred embodiments, the arms of the retractor are removably attached to the rack and pinion mechanism, such that the blades (attached to or independent of the arms) may be inserted into the sternal incision individually and independent of the rack and then later connected to a rack and pinion mechanism. This may facilitate the insertion of the blades into the sternal incision at the beginning of the surgical procedure. This embodiment is shown in FIG. 4 with respect to an embodiment having pivoting retractor arms. However, this feature can also be employed in other embodiments, such as the embodiment shown in FIG. 1.

Similar to the above described optional embodiment, the blades can be provided removably attached to the retractor arms, such that the blades may be inserted into the sternal incision individually and independent of the arms and rack and then later connected to rack and pinion mechanism. This may facilitate the insertion of the blades into the sternal incision at the beginning of the surgical procedure.

The connector 30 provides for spacing of the rigid frame of the blade 26 from the retractor arms 14, 16. The preferred distance of this spacing will vary depending upon the amount of fat anterior to the patient's sternum. The sternum may be directly under the patient's skin, thus requiring a very short connector, or there may be an inch or more of fat between the skin and the sternum. It is preferable to use as short a connector as allowed by the patient's fat layer, since otherwise the retractor attachment clip 28 and arms 14, 16 will protrude above the patient and interfere with the surgeon's access to the exposed area. Preferably, the connector length will range between 1 and 5 cm. Desirably, connectors of various lengths may be available such as at least short (1 cm), medium (2.5 cm), and deep (5 cm) connectors.

Figure 2:
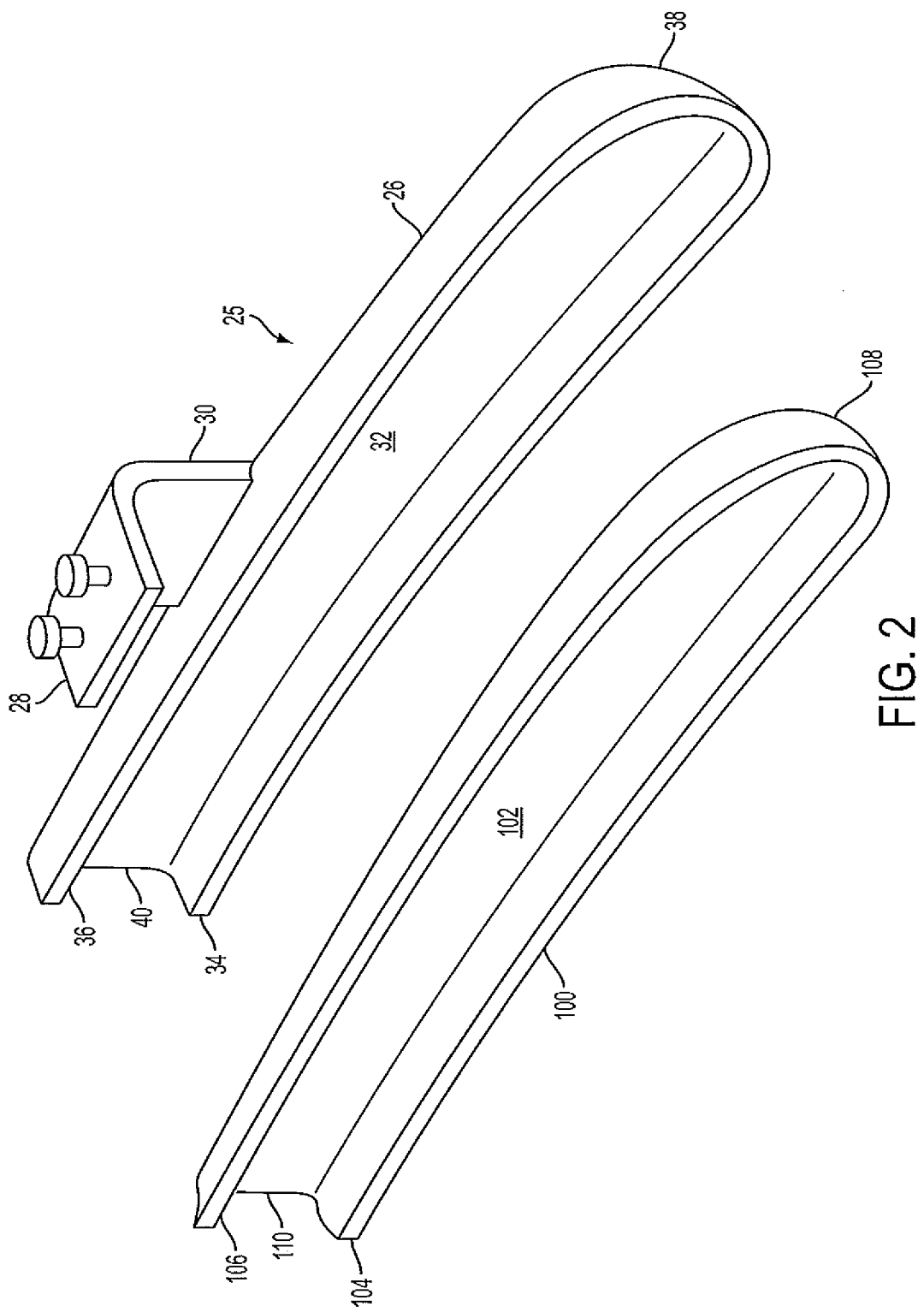
FIG. 2 is a perspective view of a retractor blade according to one embodiment of the invention showing the insert in exploded view.

In one embodiment, as shown in FIG. 2, the retractor blade 24 is a single element comprising the frame 26, connector 30, and attachment clip 28. In this embodiment, it may be desirable to provide a plurality of retractor blades having varying connector lengths and blade widths/shapes. Alternatively, the retractor blades can be provided with independent frame, connector, and attachment clip. In this case, it may be desirable to provide connectors of varying lengths so that retractor blades can be assembled having the desired combination of blade width/shape and connector length. The width of the connector may also be variable. A narrow connector will produce less contact with and subsequent traction on the skin edges, while a wider connector will result in more direct contact with and traction on the skin edges. It may be desirable to provide connectors of two widths, a narrow connector of about 1 to 4 cm and a wider connector of about 4 to 12 cm.

Figure 7:
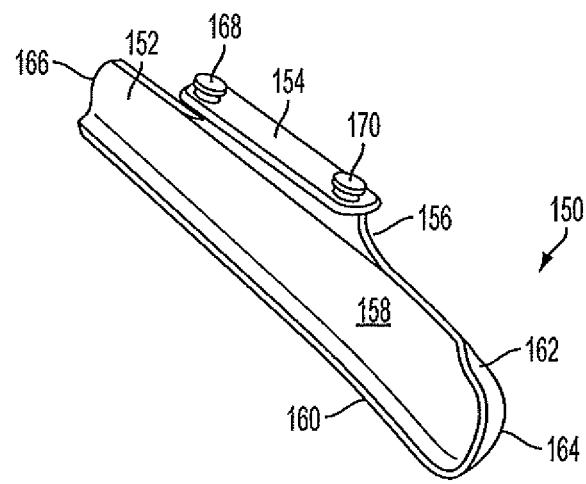
FIG. 7 is a perspective view of another embodiment of a retractor blade according to the invention.

FIG. 7 illustrates a second preferred embodiment of a retractor blade. Blade 150 includes a rigid frame 152 and an attachment clip 154. A connector 156 connects the attachment clip 154 to the rigid frame 152. The frame, connector, and attachment clip can be one integral part, two separate parts, or three separate parts.

Rigid frame 152 is sized and shaped to cover a substantial amount of the cut sternal edge. A substantial amount means that the frame extends the entire length of or at least 50% the length of the cut sternal edge. Desirably, rigid frame 152 has a "canoe" shape with a floor 158 and side wall 160. The caphalad end 164 can be closed with a wall as shown here or can be open with no wall. Caudal end 166 is preferably open as shown in FIG. 7 or can also be enclosed with a wall. Side wall 162 extends only about 5% of the length of the frame 152 as shown here. Side wall 162 can also be absent or extend the fill length of the frame. Preferably in this embodiment, side wall 162 extends about 5 to 20% the length of the frame 152.

Floor 158 can be flat or slightly bowed outward or inward. Attachment clip 154 includes two pins 168, 170 for attaching the blade 150 to a retractor arm.

In a preferred embodiment, the device and method for reducing bleeding from the cut edge of a sternum involves the use of inserts fixed to the sternal retractor blades so that when the retractor blades are placed into the sternotomy incision, the inserts contact the cut edge of the sternum forcefully as the retractor is opened and the sternal edges are pried apart. The inserts act to tamponade the blood flow from the cut sternal edge. Preferably, the inserts are sized and shaped to fit within the rigid frame of the retractor blades described herein. Thus, the inserts will have generally the same dimensions as the rigid frame. However, the insert may be sized smaller or larger than the rigid frame.

One example of an insert according to the invention is shown in FIG. 2. Insert 100 is sized and shaped symmetrically to rigid frame 26, having a similarly shaped floor 102, walls 106 and 106, closed cephalad end, 108 and open caudal end 110.

The insert 100 in the embodiment shown in FIG. 2 is simply friction fit into the frame 26. In one embodiment, the frame 26 has an inwardly directly lip (not shown) around the top perimeter and the insert 100 is retained by the lip. The insert 100 could be simply pushed into place or slid into the frame 26, from the caudal end, so that it slides under the lip.

An insert can be attached to the rigid frame 26 in a number of ways. In another embodiment, the insert can be molded to the frame 26—the frame and insert can be an integral piece. In another embodiment, the insert and frame can each have a fastening material attached thereto which bond to each other, such as Velcro® or double sided tape. Similarly, a snap-on attaching means could securely and removably fasten the insert to the interior of the rigid frame 26 of the retractor blade.

If the insert is disposable but the frame is not it is important that no part of the insert material or disposable fastener is left in or on the frame after the insert is removed.

Figure 8:
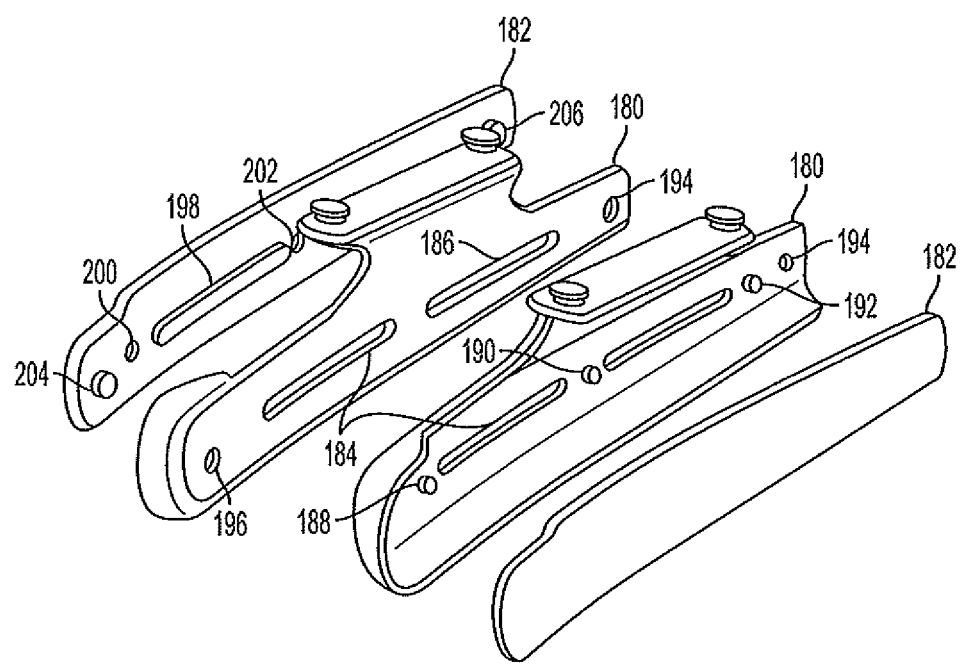
FIG. 8 is a perspective exploded view showing a preferred embodiment of the attachment of an insert to a blade.

FIG. 8 illustrates one preferred method for attaching an insert to a retractor blade frame using one or more mating protrusions and indentations. Protrusions can be in the form of pins and other elements that extend from the blade. Indentations can be in the form of holes or other receptacles. Blade 180 is illustrated in mirror image. Insert 182 is shown exploded from blade 180. Blade 180 includes elongated slits 184, 186, male pins 188, 190, 192, and female indents 194, 196. Insert 182 contains two elongated protrusions 198 (the second is not in view) which mate with blade elongated slits 184, 186; three female indents 200, 202 (the third is hidden from view) which mate with blade male pins 188, 190, 192; and two male pins 204, 206 which mate with blade female indents 194, 196.

Prior to use, the insert 182 is attached to the blade 180 by snapping the male and female elements together. After use, the insert 182 can simply be peeled off of the frame 180 and disposed. While the blade and insert are shown here having a multitude of attachment points it should be understood that the invention can employ more or less attachment points, and a different variety of attachment means (slits, tabs, extrusions, male pins, female indents, etc.).

The insert is desirably made of a material that conforms to the surface of the cut sternal edge so that a seal is created that reduces or eliminates blood flow. The cut sternal edge has a surface which is an uneven, irregular latticework of cancellous bone, containing sharp bony surfaces as well as open pores. Desirably, the insert conforms to the surface so that it tamponades bleeding from the cut surface. By conforms is meant that the insert will adjust its surface to match the surface of the sternal edge so that a maximum amount of surface area of the sternal edge is tamponaded by the insert.

In order to provide these functions, the material should exhibit a soft, rubbery, and pliant behavior. Typical materials that are appropriate have a durometer ranging from about 20 to 60 Shore00 or about 10 to 70 Shore A, more desirably between 20 and 40 Shore A. These properties minimize the risk of trauma at the material/body interface and allow for gentle removability. In addition, the insert material cannot shred on the cut bone surface or otherwise leave material on or in the surface of the sternal bone or elsewhere in the surgical incision after use. The insert is desirably made of a material that is self sealing. The insert material must be biocompatible and sterilizable. The thickness of the insert should desirably be between about 0.5 to 20 mm.

A number of different materials can be used for the insert, including silicones and thermoplastic elastomers. Other materials that may be appropriate for use include some gels, polyurethanes, and rubbers. Examples of materials include Dynaflex™ G2 706-1000-00 by GLS Corporation, Medalist® MD-110 by Teknor Apex, Elastosil® R 427/30 by Wacker Chemical Corporation, and LC 58220 by Star Thermoplastic Alloys and Rubbers, Inc., and SILASTICS 9252/250P.

In one embodiment, the insert is supplied as a material that is tastable or moldable. In other words, the insert is provided in a first state and changes state as it is applied to the cut sternal edge. For example, the material could be a material that changes state in response to a change in temperature, exposure to moisture, or upon light activation.

In another embodiment the insert is a dual material—a softer material such as a conformable gel-like material having a tougher skin. In this way the insert can function as desired as a tamponade but is protected from shredding or otherwise leaving particles upon use.

The insert may include additives such as pro-thrombic agents, antimicrobial agents, analgesic agents, and osteoblastic agents. These can be linked to the insert via known techniques or absorbed into the insert. Other methods of incorporating additives are known and can be used.

Figure 6:
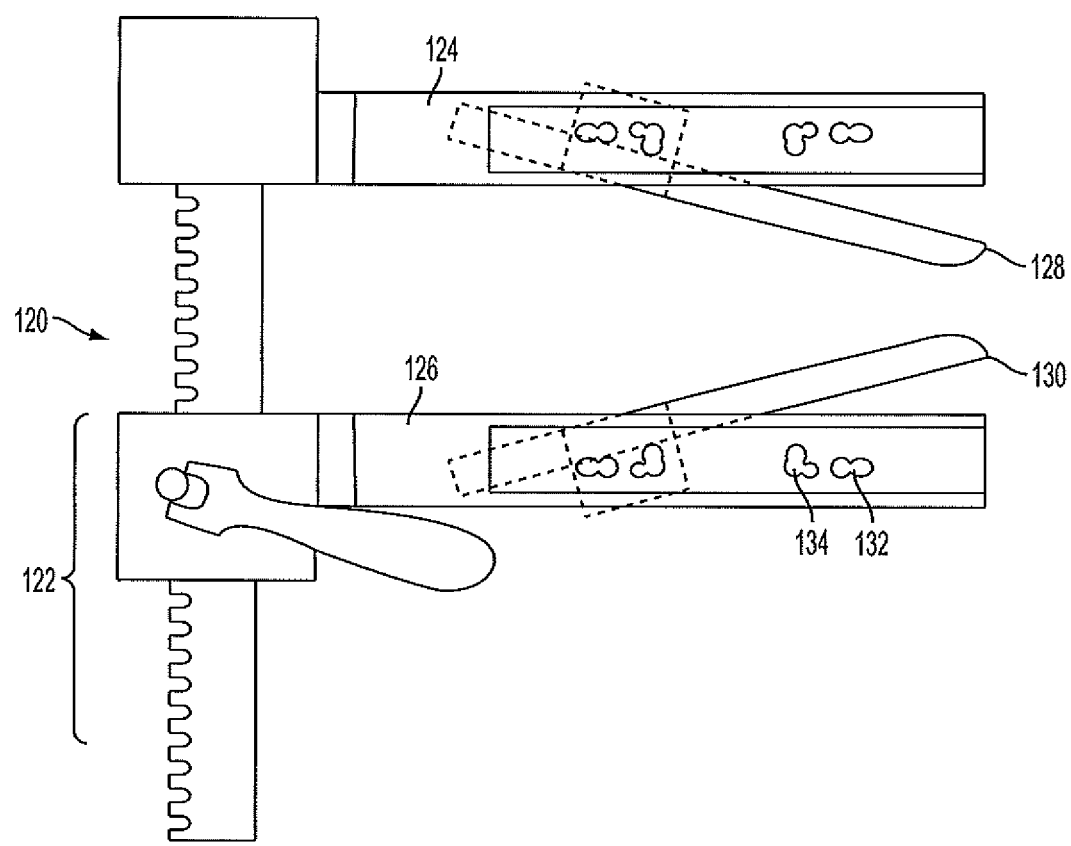
FIG. 6 illustrates an embodiment of a retractor having pivoting blades that can be reversibly employed for a patient.

It may be desirable in some cases to use the retractor in the opposite orientation than that discussed above, where the rack and pinion mechanism is cephalad to the patient rather than caudal. In this situation it may still be desirable to have retractor blades that rotate and FIG. 6 illustrates one embodiment of a retractor having this feature. Retractor 120 includes a rack and pinion mechanism 122. Retractor arms 124, 126 have retractor blades 128, 130, respectively, mounted thereon with the two pin pivot mechanism described above. In addition to the circular stationary receiving hole and the oblong shaped sliding hole as described above, this embodiment has a second set of receiving holes, a stationary receiving hole 132 and an oblong sliding hole 134. If the retractor is used in the direction having the rack and pinion at the cephalad end, the blades are mounted using this second set of receiving holes 132, 134. Other means of providing reversible retractors with pivoting arms can also be provided.

In one embodiment, one or more elements of the retractor or blade are disposable. The insert is desirably disposable. The retractor blade can also be disposable, whether it is provided as an integral piece with the frame, insert, connector, and attachment clip or whether these parts are provided individually. In another embodiment, the retractor blade can be provided as a single piece with the frame, insert, connector, and retractor arm and the entire assembly may be disposable.

Figure 9:
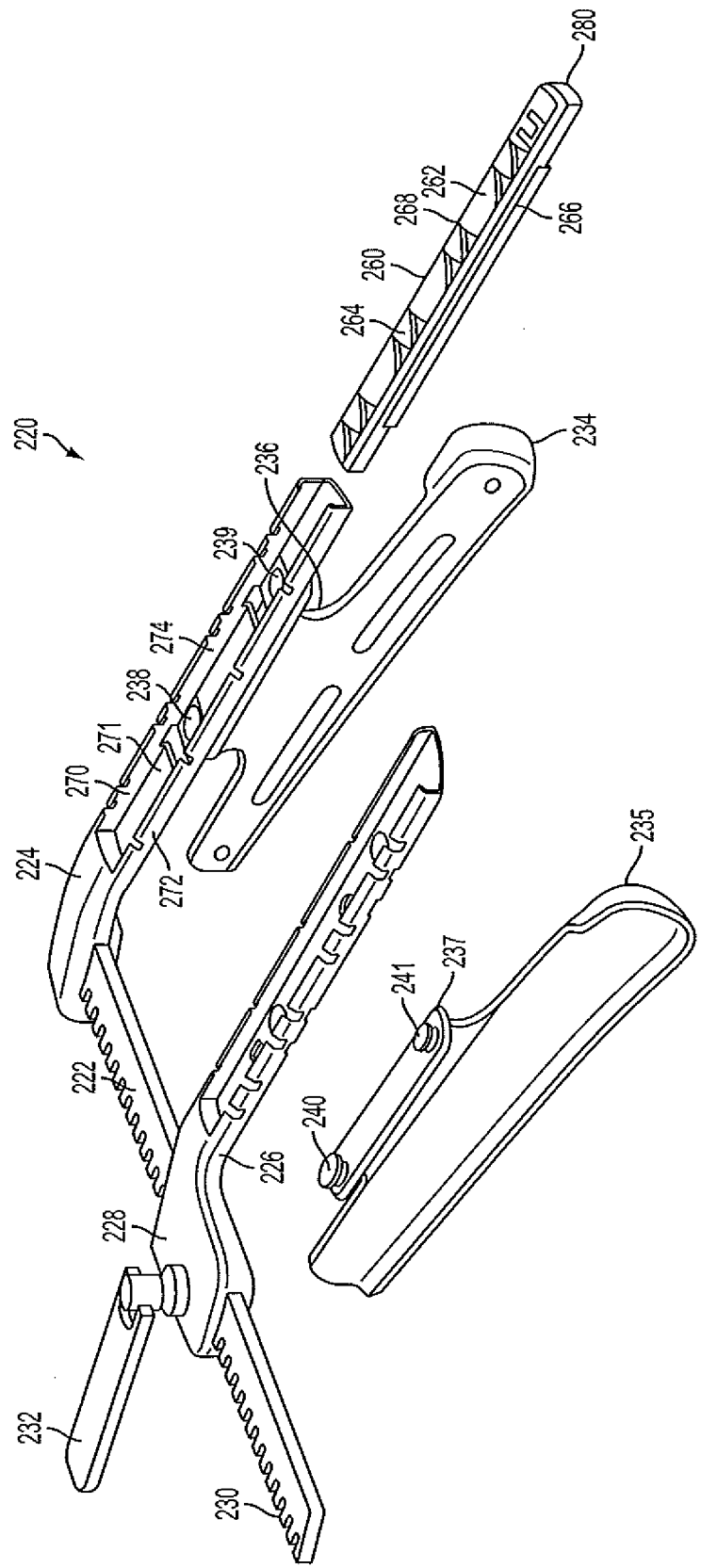
FIG. 9 is a perspective view of another embodiment of a retractor and retractor blades as described herein.

FIG. 9 illustrates another preferred embodiment of a retractor 220. The retractor 220 includes a rack 222 having a fixed arm 224 attached thereto. The rack 222 has a second movable arm 226 also connected thereto. Movable arm 226 has a housing 228 on one end thereof containing a pinion gear (not shown). This pinion gear interacts with a number of teeth 230 on rack 222, functioning as a rack and pinion gear. Rotation of the pinion gear and thus movement of the moving arm 226 along the rack 222 is controlled by knob 232.

Retractor blades 234, 235 are attached to the fixed arm 224 and the moving arm 226, respectively, through attachment clips 236, 237, respectively. Attachment clip 236, 237 each is topped with two extending pins; 238, 239 on clip 236 and 240, 241 on attachment clip 237. In a preferred embodiment, pins 238 and 240 have larger heads than pins 239 and 241. As shown more clearly in FIG. 10, retractor arm 226 includes an elongated receiving trough 242 with floor 243 and walls 244, 246. Walls 244, 246 are each topped with a retaining lip. In a preferred embodiment, wall 244 is slightly shorter than wall 246.

Four grooves are cut into floor 243, grooves 248, 250, 252, 254. Outer grooves 248, 254 are curved towards each other. In a preferred embodiment, outer grooves 248, 254 are narrower in width than grooves 248, 254 so that they can accept pins 239 and 241 but not pins 238 and 240. All grooves 248, 250, 252, 254 are open ended at the connection of floor 243 to wall 246.

Figure 10:
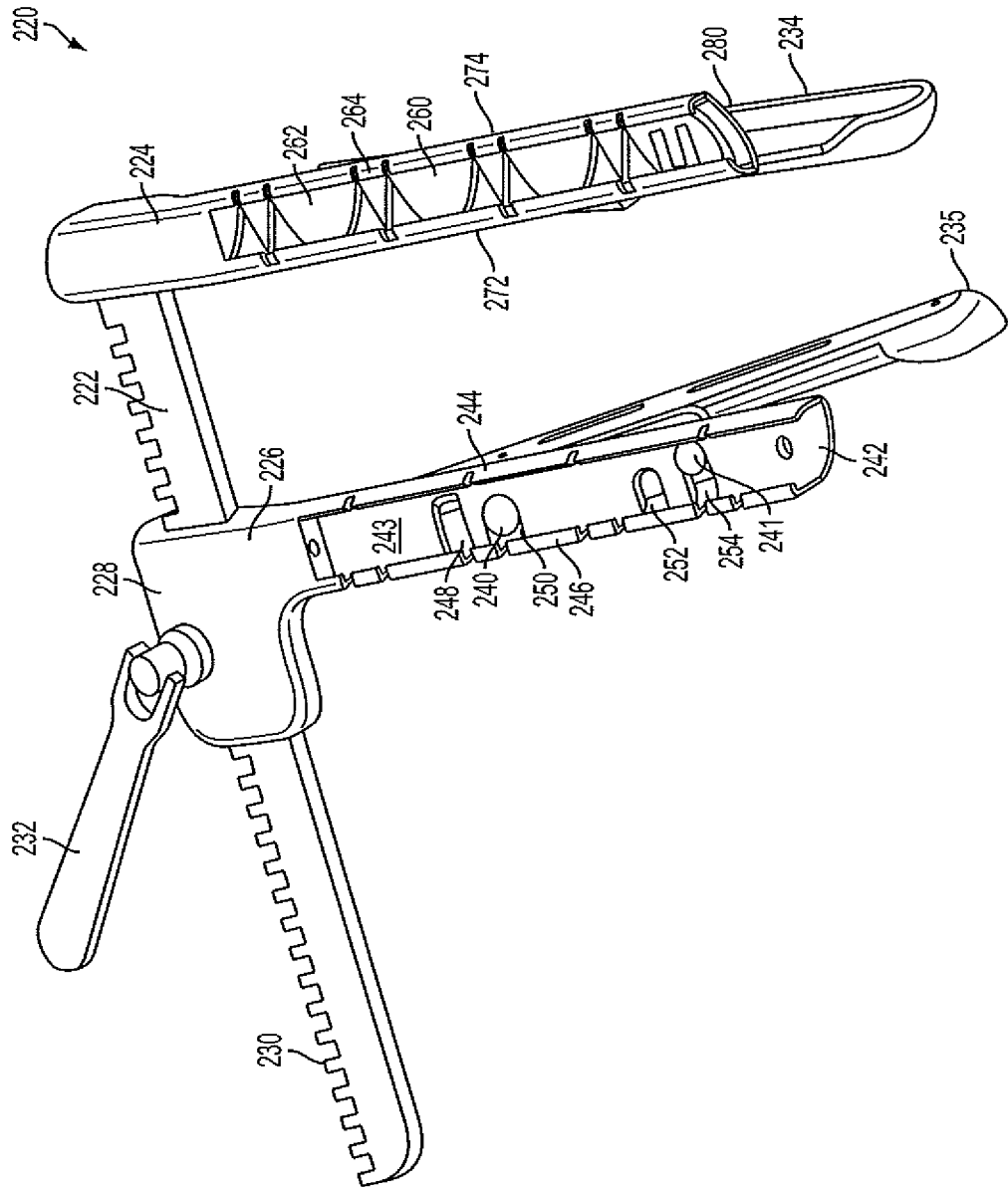
FIG. 10 is an additional view of aspects of the embodiment of FIG. 9.

To mount the blade 235 onto the arm 226 in the direction shown in FIGS. 9 and 10, the pin 240 is inserted into groove 250 and the pin 241 is inserted into groove 254. Note that in the preferred embodiment, the pin 240 will not fit into groove 248 thus ensuring the blade is mounted with the pins 240, 241 into grooves 250 and 254.

The curved groove 254 allows for pivoting of the blade 235 up to about 5°. The degree of pivot can be adjusted up to about 15° by changing the distance between the pins 240, 241, and also the distance between grooves 250 and 254.

Pins 240, 241 are prevented from slipping out of grooves 250, 254 by installation of a sliding suture guard. FIGS. 9 and 10 illustrate the suture guard 260 in relation to arm 224 and blade 234 but the principle is the same for blade 235 and arm 226. Suture guard 260 includes a body 262 having on the top surface thereof one or more suture guides 264. Left gunnel 266 and right gunnel 268 extend along the outside bottom edge of body 262. In a preferred embodiment, left gunnel 266 is slightly shorter than right gunnel 268. In a preferred embodiment, the end 280 of the suture guard 260 is curved.

Suture guide 260 can be slid into the receiving trough of arm 224. Similarly to arm 226, arm 224 includes an elongated receiving trough 270 with floor 271 and walls 272, 274. Walls 272, 274 are each topped with a retaining lip. In a preferred embodiment, wall 272 is slightly shorter than wall 274.

FIG. 9 shows blade 234 attached to the arm 224. The attachment mechanism acts the same as the previously described attachment mechanism for the arm 226 and blade 235. After blade 234 is attached to the arm 224 using pins 238 and 239, the suture guide 260 is slid into receiving trough 270. Note that in the preferred embodiment, suture guide 260 can only be inserted into arm 224, and not arm 226, since the taller right gunnel 268 of the suture guide 260 will not fit under the retaining lip of the shorter wall 272 of the arm 224. Insertion of the right-arm suture guide into the left retractor arm is, for example, prevented.

When suture guide 260 is in place the gunnel 268 blocks the pins 238, 239 from sliding out of the grooves. However, the suture guide 260 allows free pivoting movement of the pin 239 within the groove. Similarly, when the corresponding suture guide is inserted within the receiving trough of arm 226 the pins 240, 241 cannot slide out of the grooves 250, 254 but the pin 241 can freely move within groove 254 and allow pivoting of the blade 235.

Note that this embodiment of the retractor can be used reversibly, as discussed above for other embodiments. In other words, typically a sternal retractor is used with the rack towards the patient's feet. However on occasion it might be desirable to position the retractor with the rack closer to the patient's head. In this case, the blades 234, 235 can be reversed so that blade 235 is attached to arm 224 and blade 234 is attached to arm 226. In the preferred embodiment where the pin 238 is larger and the grooves 248 and 254 are smaller, blade 234 can only be positioned one way on arm 226 (with pin 238 in groove 252 and pin 239 in groove 248). Accordingly the blade will be able to pivot.

In one embodiment of the retractor and blade, there is a single pin on the blade that engages a groove on the retractor arm such that the blade can pivot on the single pin as the retractor is used to force the sternal edges apart during surgery. The location of the groove on the retractor arm is chosen to optimize the even distribution of force on the retractor blade as the retractor is cranked open. All other elements of the retractor, rack and pinion, blade and inserts could be as described elsewhere in this application. In this one-pin design, reversibility of the retractor blade is accomplished simply by switching the left and right blades on the right and left retractor arms.

The retractor is put into use after the sternum has been divided with a sternal saw or other means. In order to minimize the length of the post-operative scar, the skin incision may be made shorter than the length of the sternum. The skin incision is then undermined at its cephalad and caudal ends in order to provide access to divide the entire sternum. In this way, an incision of only 4 to 6 inches is made instead of 8 to 12 inches. However, although this shortens the length of the scar it makes more difficult the insertion of the long retractor blades of the invention into the sternotomy incision. Accordingly, the rigid frame is desirably streamlined so that it easily slides into the incision without getting caught up in the skin on either end of the incision. The frame has smooth and rounded edges and is as thin as structurally possible.

To insert the retractor, the surgeon or other operator lifts the skin at the cephalad end of the incision and slides the rigid frames of the blades 24, 25 into the incision. The frames are slid until the closed front end 38 of the frame 26 fits over the cephalad end of the manubrial bone. The skin at the caudal end of the incision can be lifted to allow insertion of the caudal end of the retractor blades. The presence of the closed cephalad end 38 or notch as described above provides tactile confirmation that the blade is properly positioned.

The method of performing a surgical procedure involving a sternotomy with less bleeding thus involves using a sternal retractor having blades that extend substantially (at least 50% and preferably at least 75%) the length of the cut sternal edge. The method further optionally involves using a sternal retractor having sternal blades including an insert that conforms to the cut sternal edge and preferably also covers substantially all of the cut sternal edge.

The method of performing a surgical procedure via a sternotomy with lower incidence of sternal fracture involves using a sternal retractor having blades that extend substantially (at least 50% and preferably at least 75%) the length of the cut sternal edge. The method further optionally involves using a retractor with pivoting blades or arms that open the sternum to provide a trapezoidal sternal opening.

The above description is for the embodiment where the retractor is fully assembled before use. As described above, the retractor may be assembled in situ. In such an embodiment, the blades, or just the rigid frame, may be first inserted into the incision and placed between the cut edges of the sternum. In some cases it may be easier to insert just the blades or rigid frame unattached to the retractor arms and rack. Preferably one blade is inserted into place over the sternal cut edge and then the other blade is placed into position. The blades are then connected to the retractor arms via one of the connecting methods described above. If the rigid frames are separate pieces they are now connected to the retractor arms via the connectors and attachment clips. In some embodiments, the retractor arms would then have to be connected to the rack and pinion mechanism.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A retractor blade for use with a sternal retractor, wherein the retractor blade comprises:
   a rigid frame configured to attach to a retractor arm; and
   an insert configured to removably attach to the rigid frame;
   wherein the rigid frame is 7 to 25 cm in length measured from a caudal end to a cephalad end; and
   wherein the rigid frame is configured to at least partially enclose a cut sternal edge and comprising:
   a floor, and
   a lower side wall; and
   wherein the insert is configured to reduce bleeding from a cut sternal edge.

2. The retractor blade of claim 1, the rigid frame comprising an end wall at the cephalad end.

3. The retractor blade of claim 2, further having a top side wall that extends from the cephalad end and has a length that is not more than 20% of the length of the rigid frame.

4. The retractor blade of claim 1, wherein the length of the rigid frame is 7.5 to 12.5 cm.

5. The retractor blade of claim 1, wherein the length of the rigid frame is 11.25 to 18.75 cm.

6. The retractor blade of claim 4, wherein the length of the insert is from 7.5 to 12.5 cm in length.

7. The retractor blade of claim 5, wherein the length of the insert is from 11.25 to 18.75 cm in length.

8. The retractor blade of claim 1, wherein a width of the rigid frame is 1.0 cm to 3.5 cm.

9. The retractor blade of claim 1, wherein the rigid frame comprises:
   a cephalad section that is 3 to 5 cm in length; and
   a caudal section that is longer than the cephalad section and that is about 4 to 20 cm in length; and
   wherein the cephalad section is at an angle with respect to the caudal section, wherein the angle is 5 to 30 degrees.

10. The retractor blade of claim 1, wherein each of the insert and the rigid frame includes one of each of one or more pairs of mating protrusions and indentations, wherein the one or more pairs of mating protrusions and indentions removably attach the insert and the rigid frame.

11. The retractor blade of claim 1, wherein the insert is conformable to a cut sternal edge.

12. The retractor blade of claim 1, wherein the insert:
   comprises a material that conforms to a cut sternal edge;
   has a durometer ranging from one of:
      20 to 60 Shore 00; or
      10 to 70 Shore A; and
   is biocompatible and sterilizable.

13. A sternal retractor comprising a first arm and a second arm and a rack and pinion mechanism to move the first and second arms away from each other and further comprising a blade of claim 1 attached to each arm.

14. A retractor blade for use with a sternal retractor, wherein the retractor blade comprises:
   a rigid frame configured to attach to a retractor arm, the rigid frame comprising a caudal section at a caudal end of the rigid frame and a cephalad section at a cephalad end of the rigid frame;
   wherein the caudal section is longer than the cephalad section, the cephalad section having a length of 3 cm to 5 cm and the caudal section having a length of 4 to 20 cm, wherein an angle between the caudal section and the cephalad section is 5 to 30 degrees;
   wherein the rigid frame has a length that is 7 cm to 25 cm wherein the length of the rigid frame includes the length of the caudal section and the length of the cephalad section;
   wherein the rigid frame comprises:
   a floor; and
   a lower side wall, wherein the rigid frame is configured to at least partially encase a cut sternal edge.

15. The retractor blade of claim 14, the rigid frame comprising an end wall at the the cephalad end.

16. The retractor blade of claim 14, further comprising a top side wall that extends from the cephalad end and has a length that is not more than 20% of the length of the rigid frame.

17. The retractor blade of claim 14, wherein the length of the rigid frame is 7.5 to 12.5 cm.

18. The retractor blade of claim 14, wherein the length of the rigid frame is 11.25 to 18.75 cm.

19. The retractor blade of claim 14, wherein a width of the rigid frame is 1.0 to and 3.5 cm.

20. The retractor blade of claim 14, wherein a width of the rigid frame tapers over the length of the rigid frame, with the cephalad end being wider and the caudal end being narrower.

21. A sternal retractor comprising:
a first arm and a second arm;
a rack and pinion mechanism to move the first and second arms away from each other; and
a retractor blade attached to each arm;
wherein a retractor blade is attached to an arm by a pin and groove mechanism which allows the retractor blade to pivot on the arm; and
wherein the pin and groove mechanism includes a first pin and a second pin on a retractor blade and a first stationary groove and a second curved groove on a retractor arm, wherein the first pin is inserted in the first stationary groove and the second pin is inserted in the second curved groove allowing the retractor blade to pivot around the first pin and groove.

22. The sternal retractor of claim 21, wherein the pin and groove attachment is reversible, such that the rack and pinion may be positioned either cephalad or caudad.

23. The sternal retractor of claim 21, wherein the each retractor blade pivots on a respective one of the retractor arms 0 to 30 degrees away from a centerline of the sternal retractor.

* * * * *